United States Patent
Hocke et al.

(10) Patent No.: US 9,247,999 B2
(45) Date of Patent: Feb. 2, 2016

(54) MICROSCOPE DEVICE

(75) Inventors: Marc Hocke, Heerbrugg (CH); Hakim El Haddouchi, Balgach (CH)

(73) Assignee: Leica Microsystems (Schweiz) AG, Heerbrugg (CH)

(*) Notice: Subject to any disclaimer, the term of this patent is extended or adjusted under 35 U.S.C. 154(b) by 817 days.

(21) Appl. No.: 13/545,347

(22) Filed: Jul. 10, 2012

(65) Prior Publication Data

US 2013/0016204 A1 Jan. 17, 2013

(30) Foreign Application Priority Data

Jul. 11, 2011 (DE) .......................... 10 2011 078 967

(51) Int. Cl.
| | |
|---|---|
| G02B 21/00 | (2006.01) |
| H01H 13/72 | (2006.01) |
| A61B 19/00 | (2006.01) |
| G02B 21/36 | (2006.01) |
| G02B 21/22 | (2006.01) |
| G06F 3/0362 | (2013.01) |

(52) U.S. Cl.
CPC .......... *A61B 19/5223* (2013.01); *G02B 21/362* (2013.01); *G02B 21/368* (2013.01); *A61B 19/26* (2013.01); *A61B 2019/2269* (2013.01); *G02B 21/0012* (2013.01); *G02B 21/22* (2013.01); *G06F 3/0362* (2013.01)

(58) Field of Classification Search
CPC ................................ G02B 21/00; H01H 13/72
See application file for complete search history.

(56) References Cited

U.S. PATENT DOCUMENTS

| | | | | |
|---|---|---|---|---|
| 5,835,266 | A | * | 11/1998 | Kitajima ........................ 359/384 |
| 2004/0036962 | A1 | * | 2/2004 | Brunner et al. ................ 359/368 |
| 2006/0081450 | A1 | * | 4/2006 | Wagener et al. ............... 200/5 A |
| 2006/0238857 | A1 | | 10/2006 | Sander |
| 2011/0038041 | A1 | * | 2/2011 | Schadwinkel ....... G02B 21/242 |
| | | | | 359/383 |

FOREIGN PATENT DOCUMENTS

| | | |
|---|---|---|
| DE | 10 2009 037 016 A1 | 2/2011 |
| GB | 2422184 A | 7/2006 |

OTHER PUBLICATIONS

Autosieger.De, "BMW: Ausstellung im Deutschen Patent—und Markenamt in München", Jul. 2008, Germany.
Elma, www.elma.com, Incremental Encoder Type E33 specification sheets.

* cited by examiner

*Primary Examiner* — Sath V Perungavoor
*Assistant Examiner* — Patricia I Young
(74) *Attorney, Agent, or Firm* — Hodgson Russ LLP

(57) ABSTRACT

A microscope device (100) includes a surgical microscope (20), a camera (30), connected to the surgical microscope (20), for sensing an object (200) imaged by the surgical microscope, a stand (10) carrying the surgical microscope (20) as well as the camera (30), an operating unit (50), spatially separated from the camera (30), for controlling device functions of the camera (30). The operating unit (30) includes a screen (40) for displaying activatable device functions (51) and a selection and activation means, embodied as an actuatable rotary/push operating means (60), for selecting and activating one of the device functions displayed. The operating unit (50) is set up such that by rotating the rotary/push operating means (60), one (52) of the displayed device functions is selected, and by pushing the rotary/push operating means (60), the selected device function (52) is activated.

7 Claims, 2 Drawing Sheets

MICROSCOPE DEVICE

CROSS REFERENCE TO RELATED APPLICATIONS

This application claims priority of German patent application number 10 2011 078 967.7 filed Jul. 11, 2011, the entire disclosure of which is incorporated by reference herein.

FIELD OF THE INVENTION

The present invention relates to a microscope device comprising a surgical microscope having a camera, and an operating unit for controlling device functions of the camera.

BACKGROUND OF THE INVENTION

Relevant microscope devices possess a stand on which the actual surgical microscope is movably arranged. The surgical microscope is usually embodied as a stereomicroscope, and in addition to one or more observation beam paths usually also possesses a so-called photo beam path, which serves to couple the object image out to a camera mounted on the surgical microscope. The camera serves for display of the object image on a screen, for image acquisition, and/or for documentation of the procedure, etc.

Operating units that possess a plurality of knobs, directional pads, etc. are used nowadays to control such medical cameras. In order to control device functions of the camera such as, for example, resolution, brightness, contrast, white balance, digital image format or video format (e.g. BMP, TIF, JPG, MPG, AVI, etc.), image or video compression methods, etc., the user or operator is forced to switch his or her attention frequently between the screen on which the device functions are displayed and the operating means; this is particularly unergonomic, time-consuming, and irritating. It creates a particularly serious disruption to an ongoing surgery.

Because this must occur under sterile conditions, the operators wear gloves, which further complicates operation.

It is therefore desirable to simplify the operation of cameras on surgical microscopes.

SUMMARY OF THE INVENTION

The solution according to the present invention allows the operation of a surgical microscope camera to be simplified, since both selection of device functions (i.e. moving to them) and activation (i.e. confirmation of the device function) are possible with a single operating means. The operating means is embodied as a rotary/push operating means, such that selection occurs by rotating, and activation by pushing.

With an operating means of this kind it is possible, for example, to eliminate a directional pad (arrow keys) as well as a selection key (i.e. a total of five keys). With a corresponding arrangement of the device functions on the screen and an adapted menu structure, the camera can be operated in its entirety using only one operating means. Reducing the control system to one operating means offers a further substantial advantage in terms of space saving as well as circuit technology.

A rotary/push operating means can, in particular, be configured to be relatively large, so that it can easily be operated even with gloves and/or can be located on the operating unit without looking. The extent vertically and/or in the push direction can be, for example, at least 2 cm. A rotary/push operating means that is both ergonomically operable and visually attractive can be made available if the extent perpendicular to the push direction is greater than in the push direction.

The rotary/push operating means is preferably spatially separated from the screen, which facilitates ergonomic arrangement of both parts.

A rotary/push operating means can be embodied particularly robustly if it comprises, for example, a one-piece knob (made, for example, of plastic or metal). It can be particularly compatible with sterility requirements in an operating room because it can be configured, for example, removably, which facilitates disinfection in particular. A preferred rotary/push operating means in this case is a knob installed removably on a sensor.

Further advantages and embodiments of the invention are evident from the description and the appended drawings.

It is understood that the features recited above and those yet to be explained below can be used not only in the respective combination indicated, but also in other combinations or in isolation, without leaving the context of the present invention.

BRIEF DESCRIPTION OF THE DRAWINGS

The invention is schematically depicted in the drawings on the basis of an exemplifying embodiment, and will be explained in detail below with reference to the drawings, in which.

DETAILED DESCRIPTION OF THE INVENTION

Figure 1:
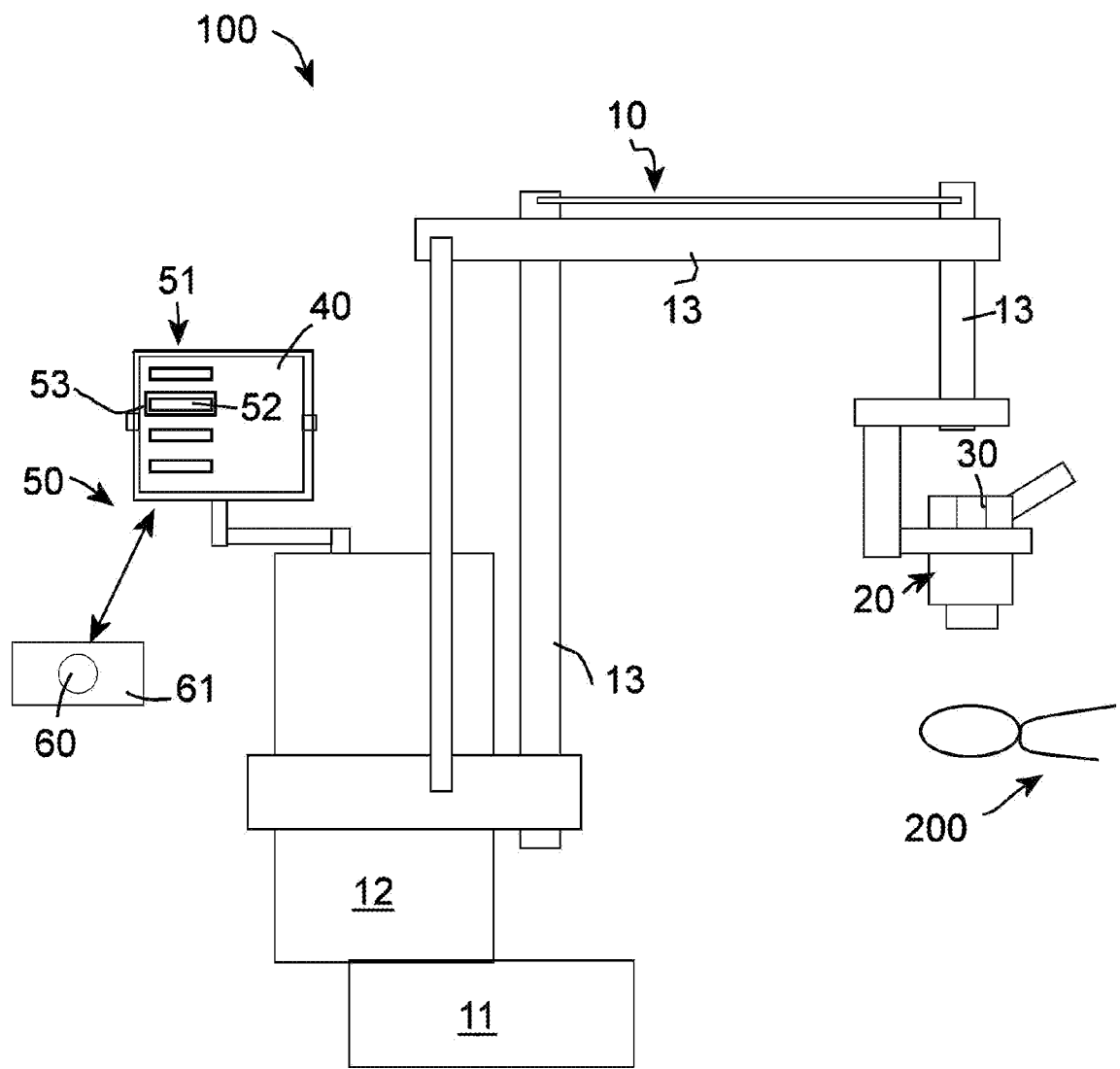
FIG. 1 schematically shows a preferred embodiment of a microscope device according to the present invention.

FIG. 1 schematically depicts a preferred embodiment of a microscope device according to the present invention, labeled 100 in its entirety. Microscope device 100 comprises a surgical microscope 20 that is carried by a stand 10 and is mounted on stand 10 movably in all three spatial directions (translationally and rotationally).

Stand 10 comprises a stand base 11 on which a stand body 12 is rotatably mounted. The stand further comprises a number of stand arms 13 that carry the surgical microscope 20 and ensure its movability in space. Arranged in stand body 12, inter alia, are components (not shown) for supplying the microscope device with electricity and the like.

A camera 30 is mounted on a photo beam path of surgical microscope 20 in order to allow sensing of an object being imaged by surgical microscope 20, for example a part (eye, brain, etc.) of a patient 200 undergoing surgery. Sensing can occur in the form of an image or video, and can be displayed on a screen 40 or the like and/or recorded.

An operating unit 50, spatially separated from camera 30, is provided for controlling device functions, for example the resolution, contrast, white balance, etc. of the camera. A wireless or cable-based connection can be provided between operating unit 50 and microscope 30, as is commonly known in the existing art. In the embodiment depicted here, screen 40 is used as a part of operating unit 50, in order to display selectable device functions 51 there (in this case in the form of a menu). For the selection and execution of a specific device function, a rotary/push operating means 60 is provided as a further constituent of operating unit 50.

In the embodiment depicted, rotary/push operating means 60 is spatially separated from screen 40 and from stand body 12, and is arranged on a holder, a housing, a panel, or the like 61. The operating means itself, or holder 61, can also be arranged on stand body 12. A wireless or cable-based connection can be provided between operating means 60 and screen 40, as is commonly known in the existing art.

Rotating the rotary/push operating means 60 causes one of the depicted device functions 51 (in the illustration, device function 52) to be selected, and pushing the rotary/push operating means 60 causes the selection to be confirmed and the selected device function 52 to be activated. The device function selected can be indicated, for example, by means of a border 53 or the like. For example, the next device function can be selected by rotating in one direction, and the previous device function by rotating in the other direction.

A rotary/push operating system is a particularly ergonomic form of control that can be executed with one hand and without looking, so that the user's attention does not need to move back and forth between screen 40 and operating means 60.

An activatable device function can also be, in particular, the display of further device functions (e.g. in the form of a submenu, main menu, or the like).

In a further embodiment, in addition to rotary/push operating means 60 a separate button or switch can be provided which activates a "cancel" device function. Upon actuation of the button or switch, an activated device function can be annulled and a higher-level (previous) device function can be re-activated, or a higher-level menu can be presented again.

Provision can also be made to implement the "cancel" device function by way of a specific actuation of rotary/push operating means 60, for example, by pushing twice quickly, by a long push, or by pulling. In such a case, device functions would then be selected by rotation, executed by normal pushing, and cancelled by a long push, double push, or pull.

In a further preferred embodiment, operating unit 50 can serve to control further microscope device functions in addition to the camera. In a surgical microscope these functions are, for example, the motion functions of the surgical microscope such as, for example, motion in X-Y but also Z (vertically), controlling the zoom (magnification function), focus, brake release and application, etc. Further functions can be the switching in or out of additional data or images, controlling additional observer outputs, blanking, or specific viewing modes (brightness, contrast, contours), etc.

Figure 2:
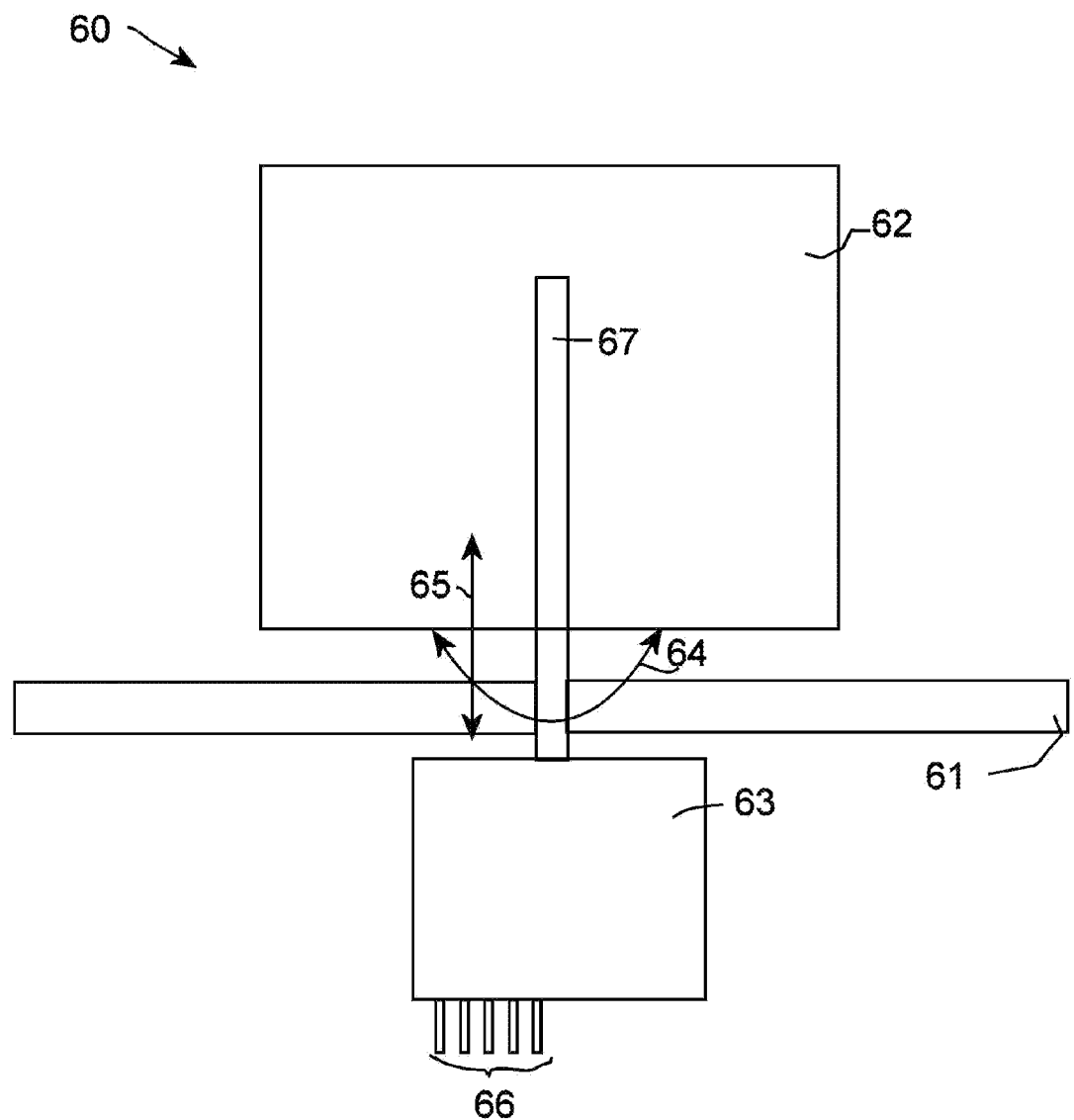
FIG. 2 is a cross-sectional view schematically showing an embodiment of a rotary/push operating means.

FIG. 2 is a schematic cross-sectional view of a preferred embodiment of a rotary/push operating means 60. Rotary/push operating means 60 is mounted on a housing 61. In the embodiment depicted here, rotary/push operating means 60 comprises a plastic knob 62 that is secured removably (e.g. by means of a clamp connection or snap connection) on a rotary/push sensor 63. Rotary/push sensor 63 possesses a rotatable and pushable shaft 67 on which knob 62 is nonrotatably secured. The rotary motion is illustrated with 64, the push motion with 65. Rotary/push sensor 63 possesses, as usual, terminals 66 for connection to an electronic circuit.

With the solution according to the present invention it is thus possible to make available a robust operating unit for the camera of a microscope device that can be operated easily, in particular with one hand and without looking, and thus in particular does not exhibit the ergonomic disadvantages recited initially. Navigation through the camera menu using previous solutions, for example arrow keys, is by contrast cumbersome, usually requires both hands, and in most cases demands at least a shift of attention from the menu being presented to the screen of the operating unit and back again. This central operating means furthermore allows the elimination of additional knobs that are otherwise necessary. This in turn provides a clearly arranged (ergonomic) operating unit.

The invention is not to be limited to the specific embodiments disclosed, and modifications and other embodiments are intended to be included within the scope of the invention.

What is claimed is:

1. A microscope device (100) comprising:
   a surgical microscope (20);
   a camera (30), connected to the surgical microscope (20), configured to sense an object (200) imaged by the surgical microscope;
   a stand (10) carrying the surgical microscope (20) and carrying the camera (30); and
   an operating unit (50) including a screen (40) displaying activatable functions (51) of the camera (30), and a knob (62) operable by a user to select and activate one of the activatable functions (51) displayed on the screen (40), the operating unit being spatially separated from the camera (30);
   wherein the knob (62) is mounted on the operating unit by a rotary/push sensor (63) such that the knob (62) is operable to select one of the activatable functions (51) displayed on the screen (40) by rotating the knob (62) and the knob (62) is operable to activate a selected one (52) of the activatable functions (51) by pushing the knob (62) in a push direction;
   wherein the knob is removably secured on the rotary/push sensor (63) by a snap connection, and at least one surface of the knob (62) is made of disinfectable material.

2. The microscope device according to claim 1, wherein the knob (62) is spatially separated from the screen (40) and arranged on a panel (61).

3. The microscope device according to claim 1, wherein the knob (62) is cylindrical.

4. The microscope device according to claim 1, wherein the knob (62) extends at least 2 cm perpendicular to the push direction.

5. The microscope device according to claim 1, wherein the knob (62) extends at least 2 cm in the push direction.

6. The microscope device according to claim 1, wherein the knob (62) extends perpendicular to the push direction a greater distance than the knob extends in the push direction.

7. The microscope device (100) according to claim 1, wherein the surgical microscope (20) is embodied as a stereomicroscope.

* * * * *